(12) United States Patent
Wildhaber (10) Patent No.: US 12,016,693 B2
(45) Date of Patent: Jun. 25, 2024

(54) APPARATUS FOR PROVIDING ELECTROCARDIOGRAM AND ARRHYTHMIA INFORMATION

(71) Applicant: Berner Fachhochschule, Technik und Informatik, Biel (CH)

(72) Inventor: Reto Andreas Wildhaber, Olten (CH)

(73) Assignee: Berner Fachhochschule, Technik und Informatik, Biel (CH)

( * ) Notice: Subject to any disclaimer, the term of this patent is extended or adjusted under 35 U.S.C. 154(b) by 1549 days.

(21) Appl. No.: 16/169,154

(22) Filed: Oct. 24, 2018

(65) Prior Publication Data
US 2019/0117103 A1 Apr. 25, 2019

(30) Foreign Application Priority Data
Oct. 24, 2017 (EP) .................................. 17 198 175

(51) Int. Cl.
  *A61B 5/367* (2021.01)
  *A61B 5/285* (2021.01)
  (Continued)

(52) U.S. Cl.
  CPC .............. *A61B 5/285* (2021.01); *A61B 5/343* (2021.01); *A61B 5/366* (2021.01); *A61B 5/367* (2021.01);
  (Continued)

(58) Field of Classification Search
  CPC ......... A61B 5/285; A61B 5/339; A61B 5/366; A61B 5/367; A61B 5/364; A61B 5/363;
  (Continued)

(56) References Cited

U.S. PATENT DOCUMENTS

| 11,331,033 B2 * | 5/2022 | Kanagaratnam ....... A61B 5/363 |
| 2004/0059237 A1 * | 3/2004 | Narayan .................. A61B 5/35 607/9 |

(Continued)

FOREIGN PATENT DOCUMENTS

WO 2017001912 A1 1/2017

OTHER PUBLICATIONS

Candes et al., "Near-Optimal Signal Recovery From Random Projections: Universal Encoding Strategies?", IEEE Transactions on Information Theory, 2006, pp. 5406-5425, vol. 52, No. 12.
(Continued)

*Primary Examiner* — Adam Z Minchella
(74) *Attorney, Agent, or Firm* — The Webb Law Firm (57) ABSTRACT

An apparatus for providing arrhythmia information uses an esophageal probe having a longitudinal axis oriented in the direction of the esophagus where it is intended to be lodged, the probe comprising at least three electrode portions spaced in the longitudinal esophageal direction of the probe. The apparatus comprises a control unit, wherein the electrode portions are connected to the control unit, wherein the control unit is configured to detect potential differences between different pairs of the electrode portions. The control unit is configured to determine a repeating heart beat pattern as basis for a time resolved determination of the potential in the direction of the longitudinal axis and possibly also a perpendicular axis of the esophageal probe using compressive sensing. The apparatus is configured to provide a plot with the representation of the activation map as observed on the posterior wall or any other wall of the heart.

23 Claims, 5 Drawing Sheets

(51) Int. Cl.
  *A61B 5/343* (2021.01)
  *A61B 5/366* (2021.01)
  *A61B 5/00* (2006.01)
  *A61B 5/363* (2021.01)
  *A61B 5/364* (2021.01)

(52) U.S. Cl.
  CPC .............. *A61B 5/363* (2021.01); *A61B 5/364* (2021.01); *A61B 5/7203* (2013.01); *A61B 5/7207* (2013.01); *A61B 5/7232* (2013.01); *A61B 2560/0468* (2013.01)

(58) Field of Classification Search
  CPC ... A61B 5/7203; A61B 5/7207; A61B 5/7232; A61B 2560/0468
  See application file for complete search history.

(56) References Cited

U.S. PATENT DOCUMENTS

| | | | | |
|---|---|---|---|---|
| 2008/0194979 | A1* | 8/2008 | Madry | A61B 5/02405 600/374 |
| 2009/0084382 | A1* | 4/2009 | Jalde | A61M 16/024 128/204.23 |
| 2011/0066381 | A1* | 3/2011 | Garudadri | A61B 5/0002 702/179 |
| 2016/0270683 | A1* | 9/2016 | Grass | A61B 18/1492 |

OTHER PUBLICATIONS

Candes et al., "Stable Signal Recovery from Incomplete and Inaccurate Measurements", Communications on Pure and Applied Mathematics, 2006, pp. 1207-1223, vol. 59.

De Ambroggi et al., "Clinical use of body surface potential mapping in cardiac arrhythmias," Anatolian Journal of Cardiology, 2007, pp. 8-10, vol. 7, Issue 1.

Donoho, "Compressed Sensing", IEEE Transactions on Information Theory, 2006, pp. 1289-1306, vol. 52, No. 4.

Marisa et al., "Asynchronous ECG Time Sampling: Saving Bits with Golomb-Rice Encoding", Computing in Cardiology, 2012, pp. 61-64, vol. 39.

Nahum et al., "Instantaneous Equipotential Distribution on Surface of the Human Body for Various Instants in the Cardiac Cycle", Journal of Applied Physiology, 1951, pp. 454-464, vol. 3, No. 8.

Niederhauser et al.,"Simultaneous Registration of ECG and Cardiac Motion by a Single Esophageal Probe", Computing in Cardiology, 2013, pp. 651-654, vol. 40.

Ramos et al., "A System for Monitoring Pill Electrode Motion in Esophageal ECG", Proceedings of the 15th Annual International Conference of the IEEE, Oct. 31, 1993, Piscataway, NJ, USA, pp. 810-811.

Zalmai et al., "Inferring Depolarization of Cells from 3D-electrode Measurements using a Bank of Linear State Space Models", IEEE International Conference on Acoustics, Speech and Signal Processing (ICASSP), Mar. 20-25, 2016, pp. 3331-3335, Shanghai, China.

* cited by examiner

APPARATUS FOR PROVIDING ELECTROCARDIOGRAM AND ARRHYTHMIA INFORMATION

CROSS-REFERENCE TO RELATED APPLICATION

This application claims priority to European Patent Application No. 17 198 175.6 filed Oct. 24, 2017, the disclosure of which is hereby incorporated in its entirety by reference.

TECHNICAL FIELD

The present invention relates to an apparatus for providing electrocardiographic and especially arrhythmia information using an esophageal probe having an longitudinal axis oriented in the direction of the esophagus where it is intended to be lodged, the probe comprising at least three electrode portions spaced in the longitudinal esophageal direction of the probe, the apparatus comprising a control unit, wherein the electrode portions are connected to the control unit, wherein the control unit is configured to detect potential differences between different pairs of the electrode portions.

PRIOR ART

The 3 lead and the 12 lead electrocardiogram (ECG) are still among the most important diagnostic tools in cardiology. Despite its popularity, common ECGs have some limitations, in particular for questions in rhythmology, due to the limited atrial (P wave) resolution.

By contrast, esophageal electrocardiography (EECG) was never widespread. Nonetheless, atrial signals of EECGs are of high amplitude and additionally provide a high signal-to-noise ratio.

There were also approaches to picture the cardiac potentials in a 2 dimensional manner. Already in 1951, L. H. Nahum, A. Mauro, H. M. Chernoff, and R. S. Sikand published in "Instantaneous equipotential distribution on surface of the human body for various instants in the cardiac cycle," Journal of Applied Physiology, vol. 3, no. 8, pp. 454-464, 1951. [Online Available: http://jap.physiology.org/content/3/8/454] published a temporal sequence of preliminary body surface potential maps with isopotential lines measured on the thorax surface, followed by other contributions refining the method as explained in L. De Ambroggi and A. D. Corlan, "Clinical use of body surface potential mapping in cardiac arrhythmias," Anadolu kardiyoloji dergisi: AKD=the Anatolian journal of cardiology, vol. 7 Suppl 1, pp. 8-10, July 2007. Nowadays techniques exist to map cardiac body surface potentials to 3 dimensional anatomical heart models; these techniques are named electrocardiographic imaging (ECGI) requesting a higher effort in equipment.

Another new approach has been made with a catheter for esophageal electrocardiography which was published under WO 2017/001912.

US 2016/270683 discloses a system for determining electrical characteristics like electrical potentials on a surface of a heart. An esophageal electrode structure measures electrical characteristics within an esophagus and a position determination unit determines the position of the esophageal electrode structure within the esophagus and the position of the surface of the heart. The electrical characteristics on the surface of the heart are then determined based on the measured electrical characteristics and based on the determined positions of the esophageal electrode structure and the surface of the heart. Since for measuring the electrical characteristics the esophageal electrode structure is used, the electrical characteristics can be measured within the esophagus and thus close to the surface of the heart, thereby allowing for an improved accuracy of determining the electrical characteristics on the surface of the heart.

SUMMARY OF THE INVENTION

In contrast to the commonly used surface electrocardiography, esophageal electrocardiography (EECG) has remained a niche application as a diagnostic method. The catheter according to WO 2017/001912 allows now to map cardiac activity to the 3 D space. Nonetheless, EECG signals have interesting qualities: As the esophagus is a long tubular structure running in close anatomical proximity to the left heart's atria, atrial signals are of high amplitude and excellent quality. These excellent signals can be displayed in a way which can be easily understood by the physician requesting examination. Furthermore, they allow the application of advanced algorithm to estimate locations of depolarization activities and to indicate the spatial and temporal development of atrial arrhythmias.

In addition, the equipment for performing esophageal electrocardiography has highly improved over the last decades. Nowadays, thin and soft catheter tubes are inserted through the nose, an already well established route from the application of feeding tubes, and reach any location along the esophagus. Local surface anesthesia is sufficient to avoid discomfort and pain during this safe and fast procedure.

An apparatus for providing electrocardiographic and especially arrhythmia information uses an esophageal probe having a longitudinal axis oriented in the direction of the esophagus where it is intended to be lodged, the probe comprising at least three electrode portions spaced in the longitudinal esophageal direction of the probe. The three electrode portions relate to the existence of at least three conducting portions within the electrode. Said electrode can be provided as a splitted electrode. The apparatus furthermore comprises a control unit, usually on the basis of a microprocessor comprising a computer program product, memory, at least sensor connections as input interfaces, and an output device as a computer screen. The at least three electrode portions of the esophageal probe are connected to the control unit, wherein the control unit is configured to detect potential differences between different pairs of the electrode portions. These potential differences are used to calculate the electrical field with a high spatial resolution in the esophagus, as well as to localize cardiac activity on the heart's surface, both using "synchronized averaging", where multiple repetitions of a signal sections are averaged with prior precise alignment, or "compressive sensing", which is a temporal or spatial undersampling of signals, which are a priori known to be sparse.

The control unit and especially the loaded or integrated computer program product are configured to initially determine a repeating heart beat pattern. A repeating heart beat pattern is either the signal of a full heart beat or the signal of only a beat fragment, which repeats a number of times. Such a heart beat pattern serves as basis for a determination of the potential in the direction of the longitudinal axis of the esophageal probe using a method which can be understood as compressive sensing, since the heart beat pattern is highly similar in its repetitions, allowing to be the base for the data acquisition on intermediate positions along the esophagus allowing representing sparse data (sampling in space is performed by the very limited number of electrode portions on the probe) in an efficient and accurate way, using sparse recovery techniques based on linear and nonlinear interpolation, usually named compressive sensing (or compressive sampling).

Compressive sensing, compressive sampling of sparse sampling is a signal processing technique by finding solutions to underdetermines linear systems and was first published by T. Tao, E. J. Candès in the article "Near-optimal signal recovery from random projections: universal encoding strategies?" published in IEEE Transactions on Information Theory, Vol. 52, 2006, pp. 5406-5425, followed by a further article by E. J. Candès, J. Romberg, T. Tao "Stable signal recovery from incomplete and inaccurate measurements" in Comm. Pure Appl. Math., Vol 59, 2006, pp. 1207-1223. An overview is published by D. Donoho as "Compressed Sensing" in IEEE Transactions on Information Theory, Vol. 52, 2006, S. 1289-1306.

Esophageal electrodes have their own characteristics: while surface electrodes stick to a particular skin location, esophageal electrodes drift inside the esophagus and their location varies with the peristalses and the patient's body and breathing motions. So esophageal electrodes, as they are usually applied, do not stick to a single location and require proper tracking of the current electrode location for any application depending on sufficient spatial resolution. Furthermore, esophageal catheters usually have a wide electrode spacing with a small number of electrodes (e.g. 8 electrodes), leading to a spatial undersampling of the field along the esophagus.

In the following, a method is presented to estimate the electric field projected onto the esophagus with a high spatial resolution. This method uses EECG signals recorded with common esophageal catheters and includes a reliable catheter position tracking to compensate for (and take use of) that catheter motion effects. This tracking gives the relative position of the catheter to the heart over time using the esophageal electrocardiogram signals only.

It was observed that solving the tracking problem solves the undersampling problem as well: the catheter's arbitrarily drifting back and forth along the esophagus axis results in a spatial sampling with small but "randomly" varying changes of the electrode (measurement) positions. As almost any ECG signal of physiologic or pathologic heart rhythms exhibit some repetitive signal patterns (e.g. repetitive atrial or ventricular waves)—the extraction of the repetitive patterns is a result of any previously applied common clustering method—synchronization between multiple heart beats is possible and, finally, refining the spatial resolution by fusing these beats using an appropriate estimate of the catheter displacement. The estimation of that catheter displacement uses the multi-channel record of the current heart beat, allowing various shifts along the esophagus axis, and compares them to the previous heart beat (e.g., by means of least square error computations), taking that shift as the estimate which gives the best match between the two beats (N. Zalmai, R. A. Wildhaber, D. Clausen and H. A. Loeliger, "Inferring depolarization of cells from 3D-electrode measurements using a bank of linear state space models," 2016 IEEE International Conference on Acoustics, Speech and Signal Processing (ICASSP), Shanghai, 2016). Extending this concept by applying it to all combinations of heart beats within a selected time frame leads to a robust estimate of the catheter displacement over the time interval of the ECG signal.

Finally, merging the multiple beats of the multi-channel ECG signal to a single high-resolution beat signal, while taking into account the time-dependent estimate of the catheter displacement, results in a high-resolution cardiac field estimate. This field estimate is presented as a two-dimensional (2D) contour plot, which is called here an esophageal isopotential map. With these contour plots the 12-lead ECG records can be complemented and addresses particular questions in rhythmology.

Solving this problem of spatially undersampled ECG signals in the way described above might also be seen as solving an "compressive sampling" or "compressive sensing" problem.

The present invention provides an esophageal potential mapping, based on signals recorded on the mucosa surface. The signals captured by the sensors relating to the electrical field are transformed in 2 dimensional spatio-temporal plots as esophageal isopotential maps (EIPMs). These maps show the projected cardiac electrical field in a graphical form with an excellent atrial resolution. This is possible through spatial sampling utilizing the natural relative movement of the esophagus, the catheter and the heart in the thorax between heart beats. In other words, the movement of the catheter in the esophagus, the movement of the patient and last but not least the inevitable movement of the heart in the thorax space, usually considered problematic by someone skilled in the art, contribute to random generator like functions and extends the e.g. eight electrode portions in twenty repetitions to about 160 position values along the longitudinal direction of the probe, bring the resolution to up to about 0.1 millimeters if the length of the probe is eight centimeters. This allows providing a high resolution esophageal isopotential map over time.

A clinical pilot study with several healthy subjects and several patients with known atrial arrhythmias showed in a qualitative comparison of the standard 12 lead ECG to the esophageal isopotential maps, that the transformation of the sensor signals into the esophageal isopotential maps provided improved spatial resolution over the traditional 12 lead ECG and an additional indication of the spatial development of atrial arrhythmias, which cannot be retrieved via the traditional way.

Further embodiments of the invention are laid down in the dependent claims.

The invention provides a three-dimensional plot of the graph with the triples (t, z, q(t, z)), with time t, location in the esophagus z, and the strength of electrical field projections, electrical potentials, or electrical potential-differences q(t, z), induced by the depolarization and repolarization in the myocardium, measured in the esophagus. The plot can be drawn in a Cartesian coordinate system. The plot is to be projected to two-dimensional space (that is to a plane) such that time t corresponds to the abscissa and location z corresponds to the ordinate. The plot is a contour plot of the potential q(t, z). Preferably, the plot is shaded in colours as a function of the potential q(t, z). It is preferable to provide a control device allowing to alter the representation of the data in two (or more) different ways relating to the time axis spanning one of two time intervals, either a short time interval for the beat view, including about a single heart systole, or a long time interval for the rhythm view, including two or more beats. It is possible to extract directly from the data the conduction speed projected to the esophagus axis via a reference scale.

The plot is overlain at various time instants with additional localized information, such as locations of cardiac triggers, conduction speed and conduction direction of cardiac depolarization wave fronts. If the control unit uses pictograms on the screen as representation at various time instants, displaying location, speed, and direction of a cardiac trigger or cardiac depolarization wave front, more physicians can easily read this data without long training periods and especially arrhythmia information is less probable to be overseen, since the high atrial signal quality, the spatial resolution of the potential development and the calculation of the wave front ensures the detection even of faint arrhythmia signals.

The apparatus is preferably configured to output a plot within a location x corresponding to the abscissa and location z corresponding to the ordinate, spanning a spatial coordinate system over a wall of the myocardium, especially the posterior wall of left-atrium of the myocardium.

The plot can comprise at least one arrow at a predetermined time being the same for any of the at least one arrow, wherein the direction of the one or more arrows is determined representing direction of an associated depolarization wave front movement on the wall of the myocardium, especially the posterior wall of left-atrium of the myocardium.

It is preferred that the at least one arrow in the plot has an attribute from the group comprising length of the arrow, width of the arrow or color of the arrow, representing the speed of the associated depolarization wave front movement. Then a person looking at this diagram can directly retrieve two relevant information: beside the direction of the associated depolarization wave which is determined by the direction of the arrow, his length or color or width can be used to retrieve further relevant information as the depolarization value.

The apparatus can be is configured to output the plot, wherein it additionally shows an estimate of the activation map as observed on the posterior wall of the myocardium.

The apparatus can further be connected to electrodes of a standard 12 lead ECG. Then one or more representations of a heart can also be positioned in the output of said standard 12 lead ECG representation and referenced to locations of cardiac triggers determined through said esophageal probe signals handled according to the present invention.

The apparatus can further be configured to provide a plot with the representation of the activation map showing the cardiac activity as observed on the posterior wall or any other wall of the heart.

The apparatus can also be configured to output a plot within a location (x) corresponding to the abscissa and location (z) corresponding to the ordinate, wherein the plot represents the cardiac depolarization front wave at various time instances.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
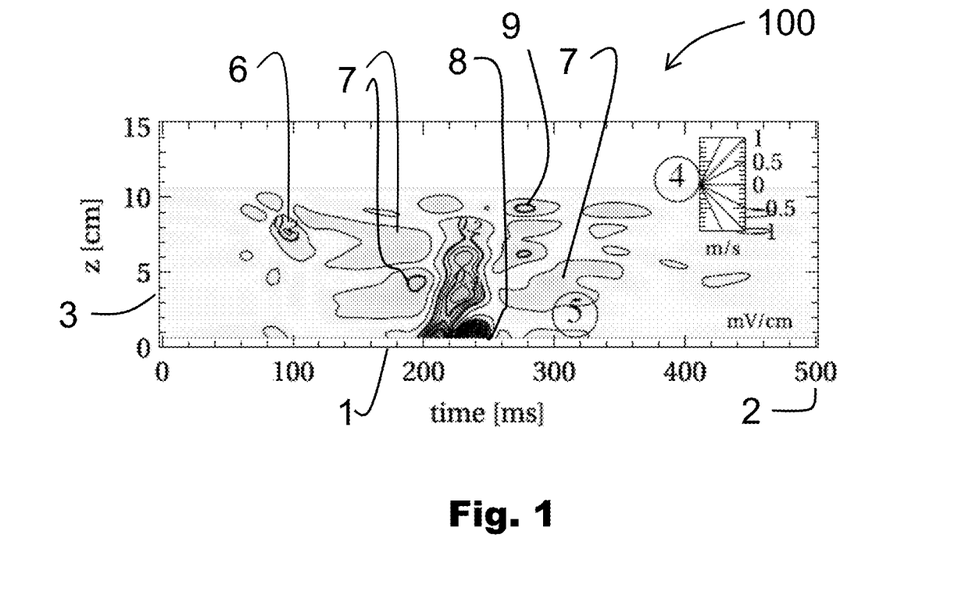
FIG. 1 shows an esophageal isopotential map (EIPM) as representation of the calculated potential result based on esophageal sensor signals.

FIG. 1 shows an example of an esophageal isopotential map (EIPM) 100 as representation of the calculated potential result based on sensor signals received from a multipolar esophageal catheter (such as e.g. described in WO 2017/001912 A1). The time axis 1 is scaled in milliseconds (ms) with a range 2 of 500 ms for beat view. Another preferred time axis range is 2000 ms for rhythm view of two or more consecutive beats as shown in the map 200 of FIG. 4.

The z-axis shows a relative esophagus position representation 3 wherein the electrical field position along the esophagus is in centimeter (cm) with increasing values for more proximal positions.

On this chart 100, isopotential lines of the electrical field are marked with the reference numeral 5, i.e. at any point in time the electrical field is calculated for a range of about 10 centimeters in the direction of the esophagus, which covers mainly the entire height of the heart's atria and the upper parts of the heart's ventricle.

Since the z-axis comprises a position information and the x-axis comprises a time representation, the direction of an isopotential line comprises within its gradient the projected conduction speed to the z-axis, wherein the conduction speed reference scale is represented and uses the reference numeral 4.

The isopotential maps 100 as shown here uses one axis only for physical position and the other axis for time evolution. This approach is possible, because the potentials are here projected onto the one-dimensional esophagus.

In other words, the esophageal isopotential map (EIPM) 100 is the graphical spatio-temporal representation of cardiac electrical potential differences measured in the esophagus. The EIPM is depicted as a 3 dimensional contour plot with time on the horizontal axis (abscissa), the esophageal location on the vertical axis (ordinate), and the electrical potential depicted as contour levels. The time axis spans the duration of a single cardiac systole and can also span approximately two or more heart beats. The esophagus location on the vertical axis is under the assumption that the esophagus follows a straight line and lays in parallel to the vertical axis of a body attached coordinate system. The electrical potential is the potential difference measured between three electrodes, both located on the esophagus mucosa, and with an interelectrode displacement along the vertical axis; a displacement of 1 centimeter is often seen. Smaller interelectrode distances are possible but technically more difficult to realize and lead to highly increased required number of electrodes. It is clear that these distances do not allow for the resolution of less than 0.2 millimeter as shown in the drawing of FIG. 1. This necessitates a specific sampling approach as explained later in this specification. The esophagus probe can also comprise more than three electrodes, further comprising only ring electrodes.

The contours are open or closed curves along which the potentials differences have constant values; these contour lines or also called iso-lines for short. The contour-level interval, that is, the elevation between consecutive lines, is for example fixed to 0.1 mV.

To enhance the readability of and to provide a uniform presentation for EIPMs, the following graphical properties are used:

1) EIPMs show the electrical field in the esophagus projected to the z-axis; the value is expressed as mV/cm.

2) The potential differences are displayed as a contour plot with respect to time (on the horizontal axis) and to esophageal location (on the vertical axis).

3) The contour-level interval is 0.1 mV.

4) Positive potential differences are shaded, preferentially in colours as yellow/red, and negative potentials can be shown in blue colors. It is possible to use thicker and thinner lines or other graphical elements to distinguish positive from negative potential maximums.

Figure 4:
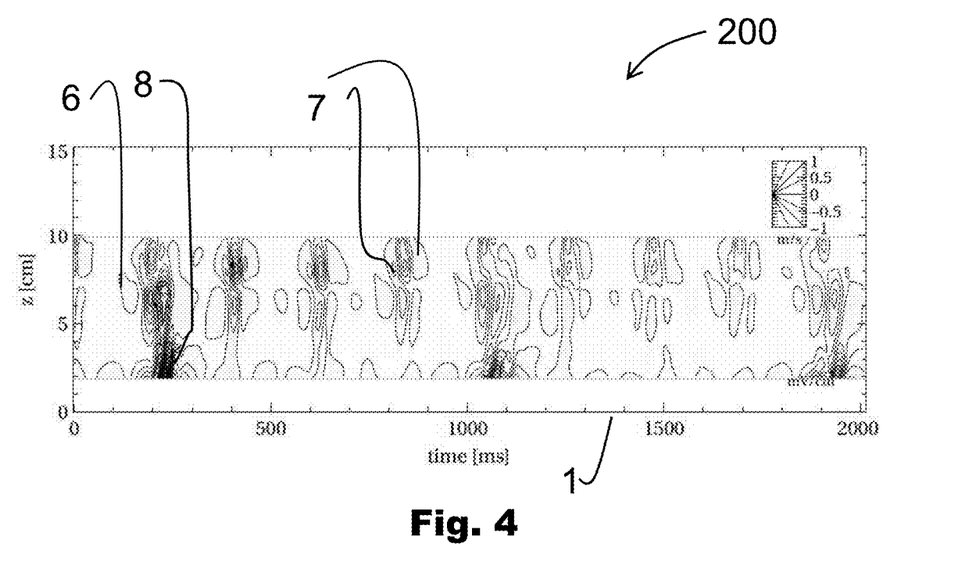
FIG. 4 shows an esophageal isopotential map (EIPM) as representation of the calculated potential result based on esophageal sensor signals similar to FIG. 1 for an extended time interval.

5) There are two different schemes for the time interval on the horizontal axis: either 500 ms (denoted as beat view and shown in FIG. 1) or 2000 ms (denoted as rhythm view and shown in FIG. 4). Each view places emphasis on different characteristics of the ECG.

6) The axes scaling of the beat view is chosen such that 1 cm on the vertical axis corresponds to 10 ms on the horizontal axis. It follows that any direction of 45 degrees reflects a propagation speed of 1 m/s.

The representation of FIG. 1 shows an atrial signal 6 at about 100 ms. It is clearly detectable through the detailed representation and has a speed of about 1 m/s downwards from the top of the atrium (e.g. sinus node) to the bottom of the atrium, the valve plane. Then, between 100 and 200 ms two small potential sinks 7 are represented. Between 200 and 240 a strong heart beat signal 8 is shown, corresponding to a ventricular excitation signal, originating near the ventricle apex, which is usually located lower in the thorax than the catheter of the esophagus testing probe can be advanced. The speed upwards is about 2 m/s. Further small potential sinks 7 and small potential increases 9 follow.

The data capturing and processing of the EECG signals is based on two distinct methods: first, the estimation of the electrical field using position resolved potentials in the direction of the longitudinal axis of the esophageal using a method similar to compressive sensing. This method works with any common esophageal catheter with at least three ring shaped electrodes and leads to an estimate of the electrical field in the esophagus with a high spatial resolution. An appropriate way to display this field estimate is the esophageal isopotential map (EIPM) as described before. The second method requires a 3 D catheter such as the catheter described in WO 2017/001912 A1 and allows the localization of cardiac activity in the 3 D space using e.g. model based approaches (N. Zalmai, R. A. Wildhaber, D. Clausen and H. A. Loeliger, "Inferring depolarization of cells from 3D-electrode measurements using a bank of linear state space models," 2016 IEEE International Conference on Acoustics, Speech and Signal Processing (ICASSP), Shanghai, 2016). Both methods can be applied and used individually. But to gain the best results (in terms of resolution) the second method should base on the field estimate of the first method and the location estimates of the second method can be used to overlay the EIPM from the first method with additional information, such as true direction and true speed information of depolarization waves. While the second method is known, the first is part of this invention and works as follows:

It is assumed to have measurements using such common esophageal catheters (remember that 3 D electrode arrangement is here not required) with sufficiently fast temporal sampling, but with a spatial sampling that seems to violate the sampling theorem due to the large electrode displacement. An electrode displacement of 1 cm, as is commonly used, is relatively large, but limited by the mechanical and construction constraints; it is too large to directly fulfill the sampling theorem along the esophageal axis, and thus seems to lead to spatial undersampling. But we take advantage from a non-ideality: The catheter is not fix to a position within the esophagus but, instead, slowly moving forth and back due to breathing and swallowing and the like. Furthermore, the position of the esophagus relative to the position of the heart is also not fixed over time. We now estimate in a first step the movement of the catheter relative to the heart, and use in a second step the estimated movement to extract the catheter, and in turn, the electrode positions and their measurements for each heart cycle. This procedure results in spatial sampling along the esophagus axis with small but arbitrarily varying electrode positions, and thus, enhances the spatial resolution as compared to the mere electrode spacing; the enhanced spatial sampling is not quite equidistant. The movement estimate bases on the comparison of pattern repetitions over multiple heart beats: a pattern is a fraction or the full record of a QRS-wave or P-wave which repeats with every heart beat. This repetitive pattern is extracted in a pre-processing step by standard signal processing clustering methods. The movement estimation then uses the multi-channel record of the current heart pattern repetition, allowing various shifts along the esophagus axis, and compares them to the previous heart pattern repetition (for example by a minimal least square error fit), taking that shift giving the best match between the two pattern repetitions. To allow a continuous displacement between the two patterns, an interpolating function is introduced to interpolate between the samples of the channels (electrodes) at each time-sample instant. This interpolation function might be a polynomial function of sufficiently high order. The comparison step comprises the comparison of multi-channel records of different heart beat patterns and outputs a shift value, wherein the shift value can be e.g. obtained determining the minimum deviation of the two heart beat patterns records e.g. using a minimal least square error fit. This concept is extended and applied to all combinations of heart pattern repetitions within a selected time frame: To not only compare and optimize between a single pair, but also over all possible pairs in said time frame, an overall cost function is defined being the sum of all cost functions of the single pairs. If said interpolation is a polynomial and the cost function is the square of the difference, the cost function for a single pair becomes a polynomial, and the overall cost function is, as a sum of polynomials again a polynomial. Continuing like this allows extracting (estimating) out of the recorded esophageal ECG signals the relative displacement of the catheter between every heart pattern repetition. Knowing the displacement (estimate) between all the heart beats allows increasing the spatial resolution along the esophagus axis by combining all records of equal pattern repetitions with their own estimated spatial location.

Figure 2:
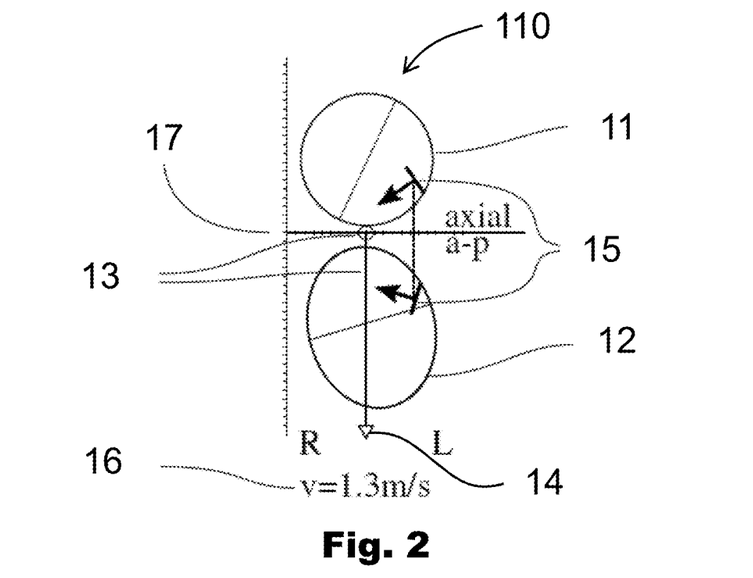
FIG. 2 shows a simplified illustration of an anatomical heart model consisting of an axial heart projection (upper part) and a frontal heart projection (lower part)

To display the additional information gained as a results of the second method in the EIPMs 100 of FIG. 1, so called augmented EIPMs, can be generated with information for overlays relating to atrial and ventricular signals for direction and speed information of cardiac depolarization wave fronts. The pictogram in FIG. 2 shows a simplified illustration of an anatomical heart model 110 consisting of an axial heart projection (upper part) 11 and a frontal (anterior-posterior, a-p) heart projection (lower part) 12. Within this heart illustration 110, true location, true speed, and true direction ("true" as opposed to "projected onto z-axis") of a cardiac depolarization wave front is marked. It is an advantage to provide such an augmented EIPM with an overlay of the pictogram, such as given by FIG. 2, onto the EIPM as given in FIG. 1, at specific time instants, i.e. around 100 ms upon detection of an atrial signal and/or around the time instant upon detection of the ventricular heart beat signal.

These time instants can either be selected by medical users or are predefined (for example at local maximal/minimal values in the EIPM: begin of atrial or ventricular activity) as explained above. The arrows 15 in the pictogram indicate the three-dimensional location, the speed, and the direction of the main depolarization front in the heart at the selected time instants. This representation extends the EIPMs 100 of FIG. 1 by the addition of true three-dimensional information for an improved arrhythmia diagnosis support. The specific averaged wave front propagation direction, starting at the source of the signal, is more accurate using the high resolution approach of the z-axis according to the invention.

Beside the heart symbol in axial view 11 with the septum and the heart symbol in a-p view 12 with the valve plane, the esophageal catheter 13 is shown in axial and anterior-posterior view, wherein the catheter tip 14 is marked with an arrow. The arrows 15 are indicating, for the same event, location, speed, and direction of main depolarization front at the given time instant. Therefore, the main direction of the depolarization front is from the left atrium towards the septum in a slightly upwards direction. As an additional output the conduction speed estimate 16 is given at the indicated location. It is noted that the axes 17 are provided with an equidistant 5 mm grid 17.

It is clear that the pictogram of the anatomical heart model 110 in FIG. 2 can be extended to include more than one arrow pair 15 to describe not only the main depolarization wave front through arrows 15 but the true wave front in more detail. It is also clear that other symbols such as an asterisk or cross (for cardiac triggers) or lines (along the wave fronts) might be introduced.

Figure 3:
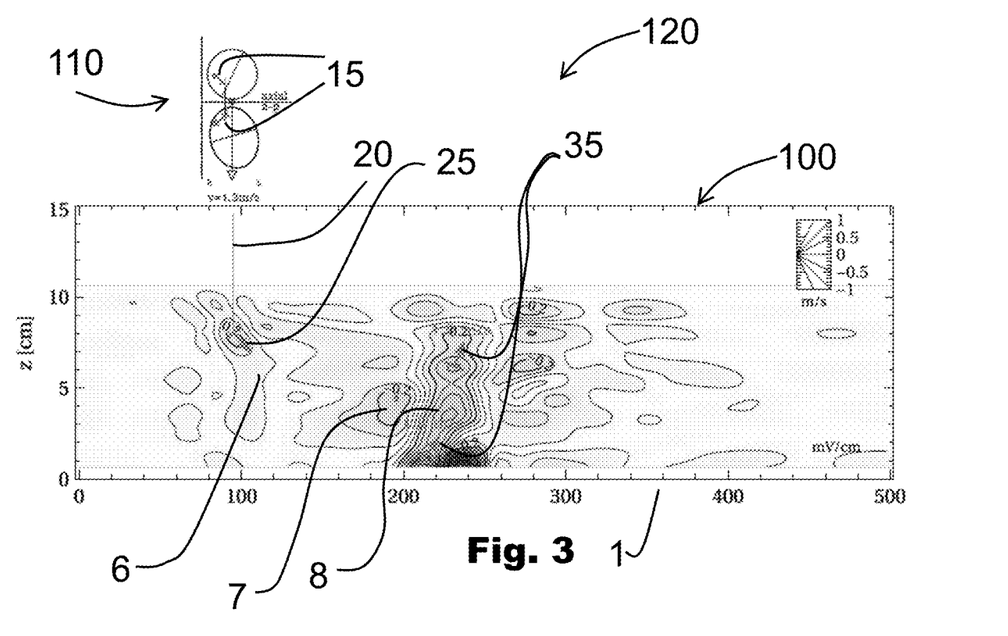
FIG. 3 shows an example of an augmented EIPM overlay as combined representation of FIG. 1 and FIG. 2.

FIG. 3 shows an example of an augmented EIPM overlay 120 with the additional information cardiac trigger locations and propagation speed, using the heart pictogram from FIG. 2. Identical features in the drawings always receive identical reference numerals.

At the time point 100 ms the pictogram of the heart with the trigger location indicated by line 20, the propagation velocity given by the speed of 1.3 m/s and the three-dimensional orientation is given by the arrow pair 15. The corresponding arrow 25 in the contour plot has a length corresponding to the true speed and a direction representing the wave front.

At the time instants 210 ms and 230 ms, further arrows 35 in the contour plot indicate main wave fronts with true speeds of 1.8 m/s and 1.9 m/s, respectively, and arrow directions indicating the orientation of these wave fronts. It is possible to provide at these time instants, or at least at one of them, a further heart pictogram 110 from FIG. 2.

FIG. 4 shows an example of an esophageal isopotential map (EIPM) 200 as representation of the calculated potential result based on sensor signals received from an esophageal catheter. The time axis 1 is scaled in milliseconds (ms) with a range 2 of 2000 ms for rhythm view of two or more consecutive heart beats. All description portions relating to FIG. 1 are applicable for FIG. 4.

Figure 5:
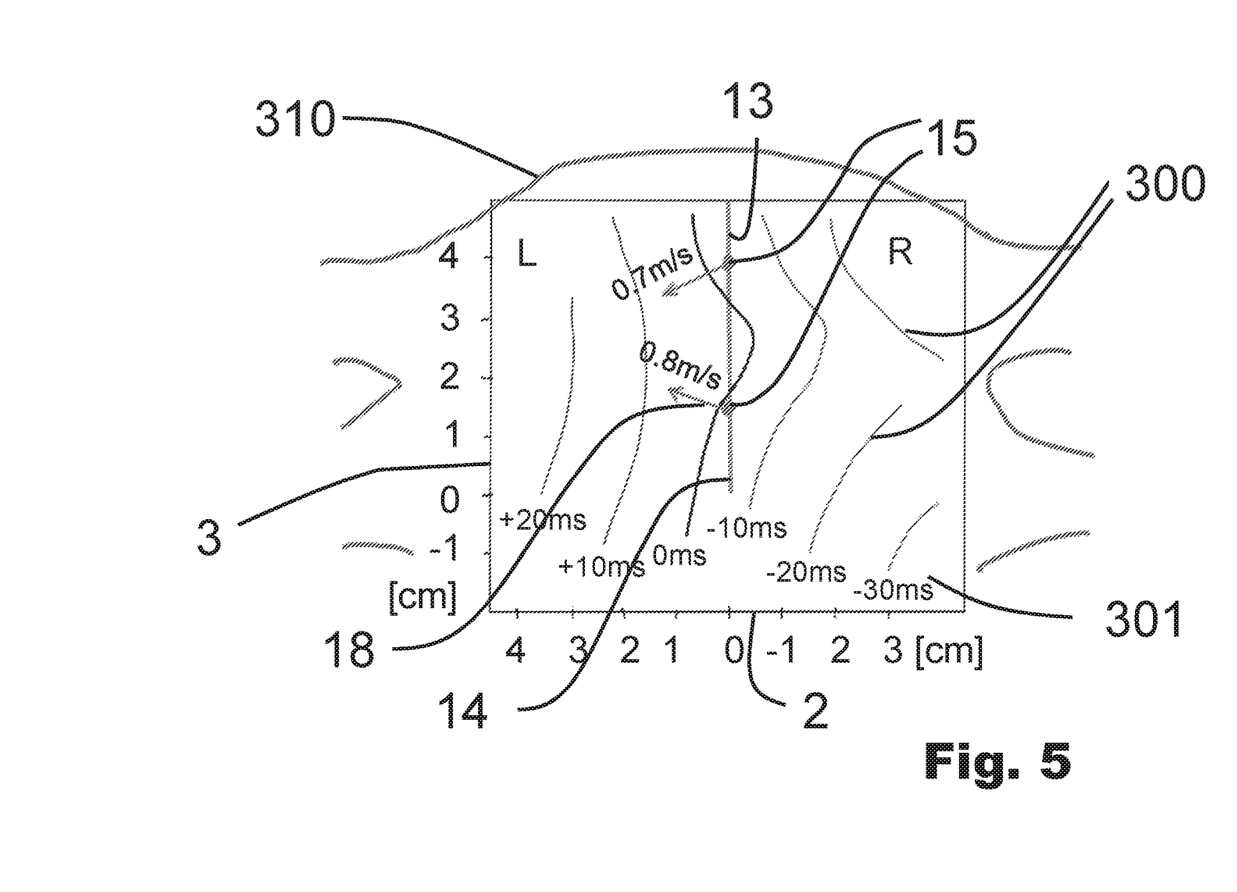
FIG. 5 shows an estimate of the activation map as observed on the posterior wall of the left atrium, whereas in FIG. 2 the main depolarization front vector in anterior-posterior is only shown as a pictogram view.

FIG. 5 shows an estimate of the activation map as observed on the posterior wall of the left atrium. An activation map displays the time evolution of the cardiac depolarization, it shows the progression of the depolarization wave front over time 300, 301. The plot has the two axis z (ordinate) and x (abscissa), spanning a Cartesian coordinate system over the myocardium of the posterior wall of the left atrium (this area is hereby assumed to be flat 310). Then, z is the location 3 on this wall surface from distal to apical (bottom to top), x is the location 2 on this wall surface from left to right. The plot is a contour plot, where each line 300 indicates the course of the activation front at a given time relative to a single heart beat cycle; this time of each line is indicted as a number next to the line 301. The direction 18 of the arrow 15 indicates the direction of the depolarization wave front. The length, width or color of the arrow indicates the speed of the depolarization wave front.

LIST OF REFERENCE SIGNS 1 time axis
2 range of x-axis representation
3 range of z-axis representation
4 conduction speed reference scale
5 isopotential lines of the electric field
6 atrial signal
7 potential sink
8 ventricular heart beat potential signal
9 small potential increase
11 axial heart projection
12 frontal heart projection
13 catheter
14 catheter tip
15 main depolarization front arrows
16 conduction speed estimate
17 grid
18 direction of main depolarization front
20 time line
25 propagation front arrow
35 propagation front arrow
100 esophageal isopotential map
110 anatomical heart model
120 augmented EIPM overlay
200 esophageal isopotential map (extended time interval)
300 activation front at given time
301 time of activation front
310 outline of posterior wall of left atrium (sketch, view from behind)

The invention claimed is:
1. An apparatus for providing arrhythmia information based on repeating heart beat pattern comprising:
an esophageal probe having a catheter and an longitudinal axis oriented in the direction of an esophagus, where it is intended to be lodged, and
a control unit,
wherein the esophageal probe comprises at least three electrode portions spaced in the longitudinal esophageal direction of the esophageal probe, wherein each of the electrode portions is connected to the control unit, wherein the control unit is configured to detect potential differences between different pairs of the electrode portions,
wherein the control unit is configured to determine a repeating heart beat pattern of a patient as basis for a determination of the potential in the direction of the longitudinal axis of the esophageal probe using compressive sensing,
wherein the control unit is configured to extract, in a pre-processing step, pattern repetitions over multiple heart beats by signal processing clustering, wherein the control unit is further configured to estimate, in a first processing step, the movement of the catheter relative to the heart based on the determined pattern repetition through arbitrary spatial sampling along the longitudinal esophageal direction of the probe due to small but arbitrarily varying catheter positions, and, in turn, electrode positions, and is configured to determine, in a second processing step, based on the estimated movement of the catheter relative to the heart, the catheter position, and in turn, the electrode position and the potential measurement for each heart cycle.

2. The apparatus according to claim 1, wherein the control unit uses data of sensed potential differences collected using multiple heart beat pattern repetitions to determine a source point of potential increases and potential sinks as well as a travelling direction and speed of a wave front of the potential increases and potential sinks for chosen specific points in time.

3. The apparatus according to claim 1, wherein the apparatus is configured to provide a 3-dimensional plot of a graph with the triples consisting of time, longitudinal location in the esophagus, and a value from the group encompassing the strength of electrical field projections, electrical potentials, and electrical potential-differences, induced by the depolarization and repolarization in a myocardium as measured through the esophageal probe in the esophagus.

4. The apparatus according to claim 3, wherein the apparatus outputs a further plot, projected to a plane such that the variable time corresponds to the abscissa and the longitudinal location corresponds to the ordinate, wherein the further plot is a contour plot of the potential.

5. The apparatus according to claim 3, wherein the time axis spans a time interval, at least one time interval from the list comprising a short time interval for a beat view, and a long time interval for a rhythm view.

6. The apparatus according to claim 3, wherein the plot comprises at least an arrow representing direction and speed of an associated potential wave front movement, wherein the arrow has its origin at the longitudinal position of the wave front at a selected time.

7. The apparatus according to claim 3, wherein a further graphical output comprises one or more representations of a heart referenced to locations of cardiac triggers, wherein the locations of cardiac triggers are displaying conduction speed and conduction direction of cardiac depolarization wave.

8. The apparatus according to claim 7, wherein the apparatus is further connected to electrodes of a standard 12 lead ECG and wherein another graphical output comprises one or more representations of a heart as output of said standard 12 lead ECG representation and referenced to locations of cardiac triggers determined through said esophageal probe signals.

9. The apparatus according to claim 3, wherein the apparatus is configured to output a further plot spanning a spatial coordinate system over a wall of the myocardium.

10. The apparatus according to claim 9, wherein the further plot is spanning the spatial coordinate system over a posterior wall of left-atrium of the myocardium.

11. The apparatus according to claim 9, wherein the plot comprises, at a predetermined time, one or more arrows, wherein a direction of the one or more arrows is determined representing direction of an associated depolarization wave front movement on the wall of the myocardium.

12. The apparatus according to claim 11, wherein the one or more arrows have an attribute representing the speed of the associated depolarization wave front movement chosen from the group comprising length of the arrow, width of the arrow or color of the arrow.

13. The apparatus according to claim 9, wherein the apparatus is configured to output an additional plot, wherein the additional plot additionally shows an estimate of an activation map as observed on a posterior wall of the myocardium.

14. The apparatus according to claim 1, wherein the control unit uses, within the estimated movement, a multi-channel record of the current heart pattern repetition, allowing for various shifts along the esophagus axis, and compares the shifts to the previous heart pattern repetition, taking that shift giving the best match between the two pattern repetitions.

15. The apparatus according to claim 14, wherein, to allow a continuous displacement between two heart patterns, an interpolating function is introduced to interpolate between the samples of the electrodes at each time-sample instant.

16. The apparatus according to claim 15, wherein the interpolation function is a polynomial function of sufficiently high order.

17. The apparatus according to claim 14, wherein, the comparison step comprises the comparison of multi-channel records of different heart beat patterns and outputs a shift value obtained determining the minimum deviation of the two heart beat patterns records.

18. The apparatus according to claim 17, wherein the control unit is configured to execute the comparison step for all combinations of heart pattern repetitions within a selected time frame covering all possible pairs in said time frame, obtaining an overall cost function being the sum of all cost functions of the single pairs.

19. The apparatus according to claim 18, wherein the control unit determines, based on the determined relative displacement of the catheter at every heart beat repetition between all the heart beats, an enhanced spatial resolution along the esophagus probe axis by combining all records of equal pattern repetitions with their own estimated spatial location.

20. The apparatus according to claim 17, wherein the comparison within the comparison step uses a minimal least square error fit.

21. A method for providing arrhythmia information based on repeating heart beat pattern comprising of a patient:
providing an esophageal probe having a catheter and an longitudinal axis oriented in the direction of an esophagus, where it is intended to be lodged; and
providing a control unit connected with the esophageal probe,
wherein the esophageal probe comprises at least three electrode portions spaced in the longitudinal esophageal direction of the esophageal probe, wherein each of the electrode portions is connected to the control unit, wherein the control unit is configured to detect potential differences between different pairs of the electrode portions,
wherein the method comprises
introducing and lodging the esophageal probe in the esophagus of the patient,
extracting, in a pre-processing step, pattern repetitions over multiple heart beats by signal processing clustering,
estimating, in a first processing step, the movement of the catheter relative to the heart based on the determined pattern repetition through arbitrary spatial sampling along the longitudinal esophageal direction of the probe due to small but arbitrarily varying catheter positions, and, in turn, electrode positions, and
determining, in a second processing step, based on the estimated movement of the catheter relative to the heart, the catheter position, and in turn, the electrode position and the potential measurement for each heart cycle.

22. The method according to claim 21, comprising the step of, based on data of sensed potential differences collected using multiple heart beat pattern repetitions, determining the source point of potential increases and potential sinks as well as the travelling direction and speed of the wave front of the potential increases and potential sinks for chosen specific points in time.

23. The method according to claim 21, comprising the step of providing a 3-dimensional plot of a graph with triples consisting of time, longitudinal location in the esophagus, and determining a value from the group encompassing the strength of electrical field projections, electrical potentials, and electrical potential-differences, induced by the depolarization and repolarization in the myocardium as measured through the esophageal probe in the esophagus.

* * * * *

UNITED STATES PATENT AND TRADEMARK OFFICE
CERTIFICATE OF CORRECTION

PATENT NO. : 12,016,693 B2
APPLICATION NO. : 16/169154
DATED : June 25, 2024
INVENTOR(S) : Reto Andreas Wildhaber It is certified that error appears in the above-identified patent and that said Letters Patent is hereby corrected as shown below:

On the Title Page

Item (54) Column 1, Title, Line 2, and in the Specification Column 1, Lines 1-3, delete "ELECTROCARDIOGRAMAND" and insert -- ELECTROCARDIOGRAPHIC AND --

Signed and Sealed this
Twentieth Day of August, 2024

Katherine Kelly Vidal
*Director of the United States Patent and Trademark Office*